US00PP26108P3

(12) United States Plant Patent
Dobres

(10) Patent No.: US PP26,108 P3
(45) Date of Patent: Nov. 17, 2015

(54) ***COREOPSIS* PLANT NAMED 'NOVACORBIR'**

(50) Latin Name: *Coreopsis verticillata*
Varietal Denomination: Novacorbir

(71) Applicant: CP DELAWARE, INC., Wilmington, DE (US)

(72) Inventor: Michael S. Dobres, Philadelphia, PA (US)

(73) Assignee: CP DELAWARE, INC., Wilmington, DE (US)

( * ) Notice: Subject to any disclaimer, the term of this patent is extended or adjusted under 35 U.S.C. 154(b) by 99 days.

(21) Appl. No.: 13/998,745

(22) Filed: Dec. 3, 2013

(65) Prior Publication Data

US 2015/0156942 P1 Jun. 4, 2015

(51) Int. Cl.
*A01H 5/02* (2006.01)

(52) U.S. Cl.
USPC ..... Plt./417

(58) Field of Classification Search
USPC ..... Plt./417
See application file for complete search history.

*Primary Examiner* — Susan McCormick Ewoldt
(74) *Attorney, Agent, or Firm* — Buchanan, Ingersoll & Rooney PC

(57) ABSTRACT

The present *Coreopsis* cultivar was created as an open-pollinated seedling of the 'Zagreb' cultivar (non-patented in the United States). A dense low compact highly uniform rounded growth habit is displayed. The plant is highly branched. Attractive, large yellow daisy-type inflorescences are formed. The green foliage coloration contrasts nicely with the yellow blossoms. The plant displays a propensity to freely flower for an extended period of time, commonly from June to September. The plant can be grown to advantage as attractive ornamentation in parks, gardens, and residential settings.

1 Drawing Sheet

Botanical/commercial classification: *Coreopsis verticillata*/Thread-leaf *Coreopsis*.

Varietal denomination: cv. Novacorbir.

SUMMARY OF THE INVENTION

Plants of *Coreopsis verticillata* sometimes bear common names such as thread-leaf *coreopsis*, whorled *coreopsis*, thread-leaved tickseed, and pot-of-gold.

The new *Coreopsis* plant of the present invention originated in a plant nursery tended by man at West Grove, Pa., U.S.A. as an open-pollinated seedling of the 'Zagreb' variety (non-patented in the United States). The exact male parent is unknown. The species likely is *verticillata*. I was attracted to a single plant of the new cultivar in view of its distinctive combination of characteristics. Had the new plant not been discovered and preserved, it would have been lost to mankind.

It was found that the new *Coreopsis* plant displays the following combination of characteristics:

(a) displays a dense low compact highly uniform rounded growth habit,
(b) displays a freely basal branching habit,
(c) displays attractive green foliage,
(d) displays a propensity to freely flower for an extended period of time commonly from June to September, and
(e) forms attractive large yellow daisy-type inflorescences.

The neat, evenly rounded growth habit that is displayed is particularly noteworthy.

The expressed combination of characteristics enables the new cultivar to be readily distinguished from its 'Zagreb' parent as well as all other previously available *Coreopsis* plants know to the discoverer. More specifically, the 'Zagreb' cultivar displays a larger, less compact growth habit. The 'Tweety' cultivar (U.S. Plant Pat. No. 23,347) forms lighter yellow blooms that are smaller in size. The 'Moonray' cultivar (U.S. Plant Pat. No. 21,931) forms light creamy ray florets and blooms that are smaller in size. The 'Moonbeam' cultivar (non-patented in the United States) forms lighter creamy-yellow blooms. The 'Star Cluster' cultivar (U.S. Plant Pat. No. 23,035) forms blooms possessing a dissimilar small purple eye. The 'Novcorcar' cultivar (U.S. Plant Pat. No. 22,565) displays blooms that are more orange in coloration combined with a dissimilar more upright growth habit.

The new cultivar can be grown to provide attractive ornamentation in parks, gardens, and residential settings.

Asexual reproduction of the new cultivar in a controlled environment by the rooting of stem cuttings has been conducted at West Grove, Pa., U.S.A. It has been demonstrated that the combination of characteristics of the new cultivar is firmly fixed and is well retained in succeeding generations. Accordingly, the new cultivar can be asexually reproduced in a true-to-type manner.

The new cultivar has been named 'Novacorbir' and will be marketed under the LITTLE BIRD trademark.

BRIEF DESCRIPTION OF THE PHOTOGRAPH

The accompanying photograph illustrates a typical flowering plant of the new cultivar at an age of approximately three years. The plant had been asexually reproduced by the use of stem cuttings and was growing in the ground in full sun at West Grove, Pa., U.S.A. The attractive yellow blossoms combined with the dense low compact highly uniform rounded growth habit are shown.

DETAILED BOTANICAL DESCRIPTION

The chart used in the identification of the colors described herein is The R.H.S. Colour Chart of The Royal Horticultural Society, London, England (1995 Edition or equivalent). In some instances, more common color terms are provided and are to be accorded their usual dictionary significance. The plants had been asexually reproduced by the rooting of stem cuttings, were approximately three years of age, and were observed while growing outdoors in the ground in full sun during October at West Grove, Pa., U.S.A.

Botanical classification: *Coreopsis verticillata.*

Cultivar: Novacorbir.

Plant:

*Habit.*—Herbaceous perennial, dense, low, compact, and highly uniformly rounded.

*Height.*—Approximately 30 to 35 cm on average. This compares to approximately 45 cm on average for the 'Zagreb' cultivar.

*Width.*—Approximately 30 to 35 cm on average. This compares to approximately 45 cm on average for the 'Zagreb' cultivar.

*Branching.*—Highly branched, commonly with approximately 35 main stems on average emerging from the soil level, and approximately 10 lateral branches on average from each main stem.

*Stem length.*—Main stems commonly are approximately 6 cm in length on average and lateral stems commonly are more variable in length with an average of approximately 8 cm on average (excluding peduncles).

*Stem diameter.*—Main stems commonly are approximately 1 cm in diameter on average and lateral stems commonly are more variable in diameter with an average diameter of approximately 5 mm.

*Stem texture.*—New growth tends to be smooth, and mature growth tends to be slightly rough.

*Stem color.*—Near Yellow-Green Group 144B overlaid with Grey-Brown Group 199B.

Foliage:

*Arrangement.*—Opposite, single, sessile.

*Shape.*—Spatulate, and sometimes narrowly-lobed (e.g., with 3 to 5 narrow lobes).

*Configuration.*—The leaves and leaf lobes are each narrowly lanceolate to linear.

*Length.*—Variable up to approximately 6.5 cm in length with lobed leaves commonly being longer than the spatulate leaves.

*Width.*—Variable, when spatulate commonly approximately 2 mm in width, and with lobed leaves commonly being up to approximately 6 cm in width across lobes.

*Apex.*—Acute.

*Base.*—Attenuate.

*Margin.*—Entire.

*Texture.*—Very finely pubescent on the upper and under surfaces.

*Venation.*—Non-conspicuous, pinnate, and of the same coloration as the foliage on both surfaces.

*Color.*—The upper surfaces of young and mature leaves commonly are near Green Group 137A, and the under surfaces of young and mature leaves commonly are near Green Group 137C.

Flowering description:

*Bud shape.*—Generally spherical.

*Bud size.*—Approximately 4 mm on average.

*Bud color.*—Grey-Brown Group 199C with the apex commonly being Yellow Group 1A just prior to opening.

*Flower appearance.*—Large daisy-type composite inflorescence form with elongated ray florets and disc florets at the center. Inflorescences are borne on terminals of lateral branches on thin peduncles. Disc and ray florets develop acropetally on a capitulum.

*Flowering response.*—Under normal conditions, plants flower from June to September in southeastern Pennsylvania, U.S.A.

*Inflorescence diameter.*—Commonly up to about 3.5 cm when fully open.

*Inflorescence depth.*—Commonly up to approximately 1.2 cm when open.

*Disc.*—Commonly up to approximately 8 mm in diameter on average.

*Fragrance.*—Slightly acrid when crushed.

*Ray florets.*—Aspect: held slightly cupped upward when opening and becoming nearly horizontal at maturity. Shape: broadly lanceolate. Length: approximately 1.4 cm on average. Width: approximately 7 mm on average. Apex: broadly acute. Base: cuneate. Margin: entire. Texture: smooth and velvety on both surfaces. Number: approximately eight arranged in a single whorl. Color: on the upper surface when opening and when mature near Yellow Group 9A, and on the under surface when opening and when mature near Yellow Group 6A.

*Disc florets.*—Arrangement: massed at the center of the inflorescence. Number: commonly approximately 22 on average. Shape: tubular, fused at the base, and flared at the apex. Length: commonly approximately 7 mm on average. Width: commonly approximately 2 mm on average at the base. Color: when fully open near Yellow Group 6A and somewhat translucent at the flared portion of the apex, and near Yellow Group 2A towards the base.

*Reproductive organs.*—Location: androecium and gynoecium present only among disc florets. Stamen number: five per floret fused into a tube surrounding the style. Anther size: approximately 2 mm in length on average and approximately 0.4 mm in width on average. Anther color: near Brown Group 200A. Pollen quantity: abundant during observations to date. Pollen color: near Yellow-Orange Group 14B. Pistil number: one per floret. Pistil length: approximately 7 mm. Style appearance: very fine. Style color: near Green-Yellow Group 1B and somewhat translucent. Stigma shape: bifid and pilose. Stigma size: approximately 2 mm on average when strongly recurved. Stigma color: commonly near Yellow Group 12A. Ovary size: commonly approximately 2 mm in length on average, and approximately 1 mm in width on average. Ovary color: near Green-White Group 157C. Receptacle size: approximately 3 mm in length on average and approximately 4 mm in diameter on average. Seeds/fruit: none encountered during observation to date.

*Involucral bracts.*—Number: commonly approximately 9 outer bracts in a row, and approximately 4 inner bracts in a row. Arrangement: the outer bracts are fused into a cone-shaped base having a length of approximately 4 mm and a width of approximately 2 mm with free apices and held slightly upward. The inner bracts surround the receptacle in a campanulate form with the apical portion unfused and spreading and held close to the ray florets. Shape: the free portion of the outer bracts is ovate, and the free portion of the inner bracts is lanceolate. Size: commonly up to 3 mm in length and 1 mm in width at the widest point. Apex: acute on the inner and outer bracts. Base: truncate on the inner and outer bracts. Texture: somewhat waxy on the inner and outer bracts. Margins: entire on the inner and outer bracts. Color: on both surfaces the outer bracts are near Yellow-Green Group 144A overlaid with Yellow Group 12A, and the inner bracts near Yellow Group 6C.

*Peduncles*.—Strength: relatively strong. Size: commonly approximately 4.5 cm in length on average, and approximately 1 mm in diameter on average. Texture: smooth. Color: commonly near Green Group 138A.

*Pedicels*.—Absent.

Disease resistance: When grown in containers, powdery mildew may need to be controlled.

Hardiness: Hardy in U.S.D.A. Hardiness Zone Nos. 5 to 9 during observations to date.

Propagation: Through the rooting of stem cuttings.

Plants of the new 'Novacorbir' cultivar have not been observed under all possible environmental conditions to date. Accordingly, it is possible that the phenotypic expression may vary somewhat with changes in light intensity and duration, cultural practices, and other environmental conditions.

I claim:

1. A new and distinct *Coreopsis* plant having the following combination of characteristics:

(a) displays a dense low compact highly uniform rounded growth habit, (b) displays a freely basal branching habit, (c) displays attractive green foliage, (d) displays a propensity to freely flower for an extended period of time commonly from June to September, and (e) forms attractive large yellow daisy-type inflorescences; substantially as illustrated and described.

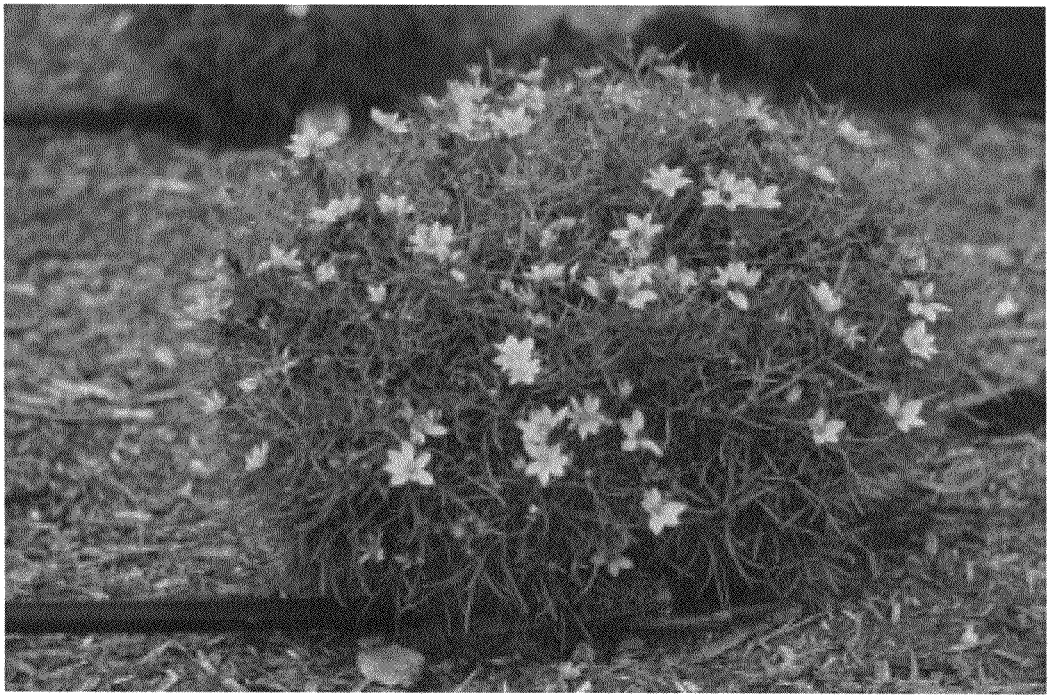

* * * * *